United States Patent [19]

Jones et al.

[11] Patent Number: 5,047,565

[45] Date of Patent: Sep. 10, 1991

[54] MONONUCLEAR AND MULTINUCLEAR PHOSPHIDO, ARSENIDO, AND STIBIDO COMPLEXES OF ALUMINUM, GALLIUM AND INDIUM

[75] Inventors: Richard A. Jones; Alan H. Cowley; John G. Ekerdt, all of Austin, Tex.

[73] Assignee: Board of Regents, the University of Texas System, Austin, Tex.

[21] Appl. No.: 108,834

[22] Filed: Oct. 14, 1987

[51] Int. Cl.$^5$ .......................... C07F 5/00; C07F 9/50; C07F 9/70; C07F 9/90

[52] U.S. Cl. .................................. 556/19; 556/20; 556/30; 556/174

[58] Field of Search ...................... 556/30, 20, 19, 174

[56] References Cited

U.S. PATENT DOCUMENTS

| | | |
|---|---|---|
| 4,464,233 | 8/1984 | Mullin et al. |
| 4,509,997 | 4/1985 | Cockayne et al. |
| 4,568,397 | 2/1986 | Hoke et al. |
| 4,591,654 | 5/1986 | Yamaguchi et al. |
| 4,599,150 | 7/1986 | Mullin et al. |
| 4,632,711 | 12/1986 | Fujita et al. |

OTHER PUBLICATIONS

Tuck, In Comprehensive Organometallic Chemistry, eds. Wilkinson, et al. Pergamon Press, New York, (1982) vol. I, Chapter 7, pp. 683–723.
Beachley, et al., J. Organometallic Chemistry, 325:69–81 (1987).
Coates & Graham, J. Chem. Soc., pp. 233–237 (1963).
Beachley & Coates, J. Chem. Soc., pp. 3241–3247 (1965).
Wells, et al., J. Organometallic Chem., 308:281–288 (1986).
Haaland, et al., J. Organometallic Chem., 322:C24 (1987).
Wells, et al., J. Chem. Soc. Chem. Commun., pp. 487–488 (1986).
Wells, et al., Inorg. Chem., 25:2483–2484 (1986).
Wells, et al., J. Organometallic Chem., 325:C7–C10 (1987).
Pitt, et al., Organometallics, 5:1266–1268 (1986).
Maury and Constant, Polyhedron, 3:581–584 (1984).
Dunphy, et al., Chemical Week, pp. 7–14 (1987).
Zweibel, C&EN Special Report, pp. 34–48 (1986).
Bradley, et al., J. of Crystal Growth, 75:101–106 (1986).
Griffiths, et al., Inaugural Meeting of the Chemicals for Electronics Panel of the Fine Chemicals Group of the CSI (1984).
Muray, et al., J. De Physique, C1:347–352 (1982).
Hamakawa, "Photovoltaic Power", pp. 87–92, undated article.
Morton Thiokol, Inc., Literature Review, article entitled "Organometallic Vapor Phase Epitaxy" (undated).
Arif, et al., J. Chem. Soc., Chem. Commun., pp. 1543–1545 (1986).

Primary Examiner—Paul F. Shaver
Attorney, Agent, or Firm—Arnold, White & Durkee

[57] ABSTRACT

The present invention involves chemical compounds particularly useful for the preparation of thin films or layers of group 3/group 5 materials by MOCVD and other techniques. Such compounds may be represented as having the formulas $[M(ER'R'')_3]_n$ or $[RM(ER'R'')_2]_n$ or $[R_2M(ER'R'')]_n$ wherein M is aluminum, gallium or indium; E is phosphorus, arsenic or antimony; R, R', and R'' are one or more of hydrogen, alkyl, aryl, alkyl-substituted aryl, cyclic alkyl, halide or other anionic group; and n is between about 1 and about 6.

9 Claims, 1 Drawing Sheet

MONONUCLEAR AND MULTINUCLEAR PHOSPHIDO, ARSENIDO, AND STIBIDO COMPLEXES OF ALUMINUM, GALLIUM AND INDIUM

BACKGROUND OF THE INVENTION

The present invention relates to new precursor compounds useful for the chemical vapor deposition (CVD) of materials which are binary combinations of group 13 elements (commonly known as group 3 elements) (Al, Ga, In) and group 15 elements (commonly known as group 5 elements) (P, As, Sb).

Organometallic compounds have been used to prepare thin films of a wide variety of materials by chemical vapor deposition. The production of compound semiconductors, metals and dielectrics has been of considerable interest. It has been known that metals and inorganic compounds can be prepared using organometallic sources, but it was felt that the materials would suffer severely from contamination from e.g. carbon, silicon and oxygen. It was not until the late 1960s that the approach of chemical vapor deposition was taken seriously. The technique known as metal-organic chemical vapor deposition (MOCVD) has since been investigated in many research laboratories throughout the world and has emerged as a powerful method for the preparation of thin films of electronic materials. A major part of the effort has concentrated on the investigation of III-V semiconductor layers, with GaAs and $Ga_{1-x}Al_xAs$ (wherein X is from 0 to 1) alloys receiving particular attention because of their commercial importance for high speed, microwave, and opto-electronic device applications. Since these materials have been studied most extensively, and because of their importance, they may be used as examples in the description of the MOCVD technique. Although the technique has not been developed to such an advanced stage for other materials, rapid progress is being made, for example, in the deposition of indium phosphide-based III-V alloys such as (GaIn)As, (AlIn)As, and (GaIn)(AsP), II-VI semiconductors, metals, and oxides.

Examples of typical reactions previously employed in MOCVD to prepare films of gallium arsenide, zinc selenide, aluminum, and tin oxide are as follows:

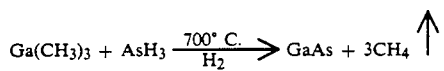

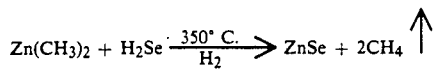

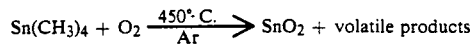

FIG. 1 schematically shows a system usable for preparation of $GaAs/Ga_{1-x}Al_xAs$ (wherein x is from 0 to 1) epitaxial layers by MOCVD. In this particular schematic example, trimethyl gallium, trimethyl aluminum, and arsine have been used to prepare gallium arsenide or gallium aluminum arsenide, with hydrogen selenide and diethyl zinc serving to dope the materials n-type or p-type respectively. The prior organometallic precursors are liquids (or, less frequently, solids) and can be transported to a reactor by bubbling a carrier gas through the liquid which is held at an accurately controlled temperature to ensure a constant vapor pressure. By precisely metering the flow of the carrier gas, hydrogen, using a mass flow controller, the concentration of the organometallic precursor in the vapor phase can be reliably and reproducibly controlled. Electronic grade organometallic precursors are usually supplied commercially in bubblers manufactured in stainless steel, whereas the hydrides are available as gas mixtures in hydrogen. The reagents generally enter the quartz reactor in the gas phase and flow over, for example, a single crystal GaAs or silicon substrate which is situated on a temperature controlled graphite susceptor heated by radio frequency induction. Deposition can be carried out at atmospheric or reduced pressure (e.g. 0.1 Atm).

Epitaxial growth of the semiconductor layer occurs at growth rates which usually lie in the range $500Å-1000Å/min$, and layer thicknesses in the range $10Å-100\mu m$ can be achieved. Materials can be doped n-type or p-type in the range $10^{15}-10^{19}$ cm$^{-3}$. In modern systems the reagents are introduced using a gas manifold which allows rapid switching of gas flows so that abrupt changes in alloy composition or doping can be achieved. The sequencing of events is controlled by computer and this allows the fabrication of complex heterostructures. The versatility of the technique makes it attractive for the preparation of epitaxial material for conventional device structures as well as the more advanced low dimensional solids such as quantum wells and superlattices.

MOCVD has been used to prepare virtually all of the possible III-V binary compounds (Al, Ga, In/N, P, As, Sb and a variety of ternary and quaternary materials such as $Ga_{1-x}In_xAs$ and $Ga_{1-x}In_xAs_{1-y}Sb_y$ (wherein x and y are each 0 to 1) compounds and alloys of the III-V type prepared by MOCVD are as follows:

| | Binary compounds | | |
|---|---|---|---|
| AlN | AlP | AlAs | AlSb |
| GaN | GaP | GaAs | GaSb |
| | InP | InAs | InSb |
| | Ternary compounds | | |
| $Ga_{(1-x)}Al_xAs$ | $Ga_{(1-x)}In_xAs$ | | $Al_{(1-x)}In_xAs$ |
| $Ga_{(1-x)}In_xP$ | | | |
| $GaAs_{(1-y)}P_y$ | $GaAs_{(1-y)}Sb_y$ | | $InAs_{(1-y)}P_y$ |
| | Quaternary compounds | | |
| | $Ga_{1-x}In_xAs_{1-y}P_y$ | | |
| | $Ga_{1-x}In_xAs_{1-y}Sb_y$ | | |

Exemplary reagents which have been used in such preparation of III-V compounds and alloys are as follows:

| Metal alkyls |
|---|
| $Ga(CH_3)_3$, $Ga(C_2H_5)_3$ |
| $Al_2(CH_3)_6$, $Al(C_2H_5)_3$ |
| $In(CH_3)_3$, $In(C_2H_5)_3$ |
| Hydrides & Group V alkyls |
| $NH_3$, $AsH_3$, $PH_3$, $As(CH_3)_3$, $P(CH_3)_3$, $Sb(CH_3)_3$ |
| Adducts |
| $(CH_3)_3In: P(CH_3)_3$ $(CH_3)_3In: P(C_2H_5)_3$ |
| $(CH_3)_3In: N(CH_3)_3$ $(CH_3)_3Ga: P(C_2H_5)_3$ |
| $(CH_3)_3Ga: As(CH_3)_3$ |
| Dopants |
| p-type $Zn(CH_3)_2$, $Zn(C_2H_5)_2$, $Cd(CH_3)_2$, |
| $Mg(C_5H_5)_2$, $Be(C_2H_5)_2$ |
| n-type $SiH_4$, $Si_2H_6$, $Sn(C_2H_5)_4$, $GeH_4$, $Sn(CH_3)_4$. |

-continued

H$_2$S, H$_2$Se, Te(C$_2$H$_5$)$_2$
Semi-insulating
Cr(CO)$_6$, VO(OC$_2$H$_5$)$_3$, Fe(C$_5$H$_5$)$_2$ It is extremely important that the reagents are free from contaminants which, if they become incorporated in a semiconductor layer, can have an adverse influence on the electrical and optical properties of the material. Purity levels well below 1 ppm have to be achieved if background carrier concentrations in the semiconductors are to be 10$^{14}$ cm$^{-3}$ or less, and methods of improving the purity of the precursors are being intensively investigated. Unfortunately, methods of analysis of impurities at these levels are proving to be somewhat difficult, they are generally assessed by study of the electrical properties of the completed film.

Listed below are the properties required of an organometallic precursor under ideal circumstances:

- Its vapor pressure should be greater than 10mm at room temperature or below. This is not essential since many of the adducts used for III-V deposition have lower vapor pressures. However, providing the compound is thermally stable it is simpler in practice not to have to heat all the gas lines and valves in the gas handling system to prevent condensation of reagents from the gas phase
- It is preferable that the organometallic compound be liquid at the temperature used. There is evidence to suggest that when a solid reagent is used the pickup is variable and this is possibly caused by the changing surface area of the solid as it is consumed.
- The impurity content of the precursor should be well below a level of 1 ppm. At the moment, the simplest way of testing the quality of a reagent is to prepare a semi-conductor layer and assess its electrical and optical properties. A great deal of time could be saved if a high sensitivity analytical technique could provide fast characterization of precursors
- Non-pyrophoric compounds would be preferable, so that fire hazards could be minimized. The majority of precursors in current use are pyrophoric, and it seems likely that this will continue to be the situation
- Reagents have to be stable in their containers over a period of years since their rate of consumption is rather low (100 gms is a typical quantity contained in a bubbler). If vapor phase concentrations of reagents are to remain reproducible from day to day and month to month, chemical changes within the containers are unacceptable
- The container in which the precursors are delivered must be designed in such a way that they can be dispensed simply and without hazard.

Metal-organic chemical vapor deposition has emerged as a powerful technique for the preparation of materials for III-V and II-VI electronic devices, and the research currently being undertaken on the preparation of oxides and metals by thermal and photolytic processes is likely to extend the range of applications of materials prepared using the technique. As the range expands there will be an increasing need for a wider variety of electronic grade organometallic precursors. The present invention involves w improved precursors and corresponding reduced and controlled impurity levels in electronic grade organometallic reagents.

Despite their potential importance as precursors to semiconductors such as gallium arsenide and indium phosphide, relatively little is known about compounds featuring bonding between the heavier group 13 and 15 (Olander numbering) elements. (Tuck in Comprehensive Organometallic Chemistry, eds. Wilkinson, et al. Pergamon Press, New York, (1982) vol. 1. ch. 7. pp. 683–723). Pioneering work by Coates et al. revealed that secondary phosphines and arsines undergo thermal reactions with Me$_3$Ga or Me$_3$In to afford materials of composition (Me$_2$MER$_2$)n, (when R=methyl (Me) n=3 and when R=phenyl [Ph], n =3; M =Ga or In; E =P or As). (Coates et al., J. Chem. Soc., (1963) 233; Beachley et al., J. Chem. Soc., (1965) 3241). Until recently, no structural information was available for compounds featuring direct sigma bonding (as opposed to dative bonding) between the heavier group 13 and group 15 elements.

Wells, et al., have reported the X-ray structure of the dimer [(Me$_3$SiCH$_2$)$_2$AsGaPh$_2$]$_2$ which is obtained via the reaction of (Me$_3$SiCH$_2$)$_2$AsH with Ph$_3$Ga (J. Organometallic Chem. (1986), 308, 281). Beachley, et al., have reported the structure of the dimeric indium phosphide complex [(Me$_3$SiCH$_2$InPPh$_2$]$_2$ (J. Organometallic Chem. (1987), 325, 69).

Other structural information comes from a gas phase electron diffraction study of the trimeric aluminum phosphide [Me$_2$AlPMe$_2$]$_3$ (Haaland, et al., J. Organometallic Chem. (1987) 322, C24). More recently, Wells, et al., have reported the novel gallium-arsenic cluster. [(PhAsH)(R$_2$Ga)(PhAs)$_6$(RGa)$_4$] (R=Me$_3$SiCH2) (Wells, et al. J. Chem. Soc. Chem. Commun. (1986), 487.

The structures of the monomeric and dimeric tris(arsino) gallanes [(Mesityl)$_2$As]$_3$Ga and {[(Me$_3$SiCH$_2$)$_2$As]$_3$Ga}$_2$ have also recently been reported (Wells, et al., Inorg. Chem. (1986), 25, 2484, and J. Organometallic Chem. (1987), 325, C7).

The synthesis of [[(Me$_3$SiCH$_2$)$_2$As]$_2$GaCl]2 has recently been reported (Pitt, et al. Organometallics, (1986), 5, 1266). The trinuclear derivatives [Et$_2$M-PEt$_2$] (M=Ga, In) and [Cl,MeGa-PEt$_2$]$_n$ (n=2.6) have also been described (Maury, et al., Polyhedron, (1984), 3, 581).

Figure 1:
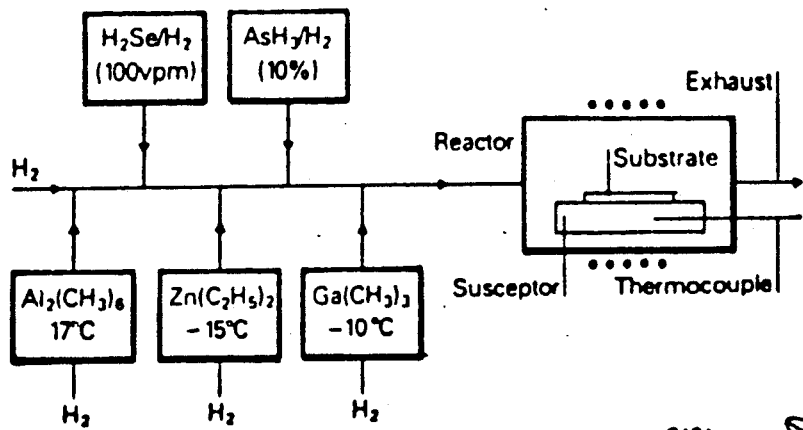
FIG. 1 is a schematic diagram of a GaAs/Ga$_{1-x}$Al$_x$As MOCVD system.

2.467(5), Ga(1)-P(1) 2.481(3), Ga(1)-C(1) 2.024(10), Ga(1)-C(2) 2.016(11), P(1)-C(3) 1.910(9), Ga(1)-P(1)-Ga(1,) 93.5(1), P(1)-Ga(1)-P(1,) 86.5(1), P(1)-Ga(1)-C(1) 115.8(4), P(1)-Ga(1)-C(2) 116.8(4), C(1)-Ga(1)-C(2) 106.3(5), C(3)-P(1)-C(7) 111.1(5).

SUMMARY OF THE INVENTION

The present invention involves chemical compounds particularly useful for the preparation of thin films or layers of group 3/group 5 materials by MOCVD and other techniques.

Such compounds may be represented as having the formulas $[M(ER''R'')_3]_n$ or $[RM(ER'R'')_2]_n$ or $[R_2M(ER'R'')]_n$ wherein M is aluminum, gallium or indium; E is phosphorus, arsenic or antimony; R, R', and R'' are one or more of hydrogen, alkyl, aryl, alkyl-substituted aryl, cyclic alkyl, halide or other anionic group; and n is between about 1 and about 6.

A preferable compound with the formula $[R_2M(ER'R'')]_n$ is where M is aluminum, gallium or induim; E is phosphorus, arsenic or antimony; R is preferably an alkyl such as methyl, n-butyl or t-butyl, or a cyclic alkyl such as cyclopentyl or cyclohexyl; when R' is R'' they are preferably t-butyl, or R' is t-butyl and R'' is H, or R' is cyclopentyl and R'' is H, and n is preferably 2. A preferred alkyl is one comprising between three and about twelve carbon atoms.

With a compound of the present invention having the formula $M(ER'R'')_3$, where M is preferably gallium or indium, E is preferably phosphorus or arsenic and R' and R'' are preferably alkyl. One particularly preferred embodiment of the compound has the formula M(ER'R'') where M is gallium, E is phosphorus, R' and R'' are t-butyl. In another preferred embodiment M is gallium, E is phosphorus R' is hydrogen and R'' is an alkyl-substituted aryl, the most preferred alkyl-substituted aryl being 2, 4, 6-tritertbutylphenyl.

DESCRIPTION OF PREFERRED EMBODIMENTS

The new precursor compounds are of general formula $[M(ER'R'')_3]_n$, or $[RM(ER'R'')_2]_n$ or $[R_2M(ER'R'')]_n$ M is aluminum, gallium or induim; E is phosphorus arsenic or antimony; R, R', and R'' are one or more of hydrogen, alkyl, aryl, alkyl-substituted aryl, cyclic alkyl, halide or other anionic group; and n is between about 1 and about 6. An important difference between these precursors and those of others that are employed in the MOCVD (metalloorganic chemical vapor deposition) process is that they feature direct sigma bonding between the group 13 and 15 elements. Previously, MOCVD methods have included the use of compounds containing a dative donor-acceptor type of linkage known commonly as "adducts" or more simply mixtures of compounds which contain the appropriate elements in different molecules. There has been one compound reportedly used for the MOCVD of thin films of GaP. This compound is $[Et_2Ga-PEt_2]_3$ (Maury, et al., *J. de Physique*, 1982, Cl, 347). Polycrystalline layers of GaP were obtained between 650° and 775.C.

The different type of bonding featured in the new compounds makes them far more stable to air and moisture than either the adducts or mixtures of compounds. The new compounds are also volatile, hydrocarbon soluble, and not appreciably toxic. The extreme toxicity and pyrophoric nature of some compounds currently used such as $AsH_3$ and $GaMe_3$, represent major environmental health problems in their use for the manufacture of materials such as GaAs.

The new compounds contain the elements required for the formation of materials within the same molecule. This feature permits the precise control of stoichiometry for the elements in the vapor phase (e.g. for $[Me_2Ga(t-Bu_2As)]_2$ Ga:As=1:1). This is not possible using mixtures of compounds without careful physical control of the components of the mixture. Although it is possible using adducts, these have the disadvantage that they may disassociate readily in the vapor phase and thus control of stoichiometry under the operating conditions is lost.

Significant advantages of MOCVD processes are apparent using the new compounds of the present invention. Such processes may be used for the formation of thin layers of materials having a group 13/group 15 composition of 1:1 in a safer and easier manner than so far possible using other compounds.

Thin layers of GaAs, for example, may be deposited on the face of silicon 100 using hydrogen carrier gas in the pressure range of 2 to 10 mm Hg using as precursors compounds such as those having the general formula $[R_2M(ER'_2)]_2$ where M is Ga, E is As, R, is Bu$^t$, R is methyl and n is 2.

Using this compound with the saturation temperature at 110° C. and reactor temperature at 475 C, a film of GaAs with a thickness of 4660 Å may be grown over a period of 5.75 hours. The carbon content of this film was less than 1000 ppm according to XPS analysis. With the saturation temperature of 100° C. and reaction temperature at 500° C., a film having a thickness of 1670 Å may be grown over a period of 4.5 hours.

In the synthesis of a prototypical compound of the present invention, the reaction of $GaCl_3$ or $InCl_3$ with three equivalents of $Bu^t_2PLi$, $Bu^t_2AsLi$, or ArP(H)Li (Ar=2,4,6-Bu$^t_3$C$_6$H$_2$) was found to afford Ga(PBu$^t_2$)$_3$, Ga(AsBu$^t_2$)$_3$, and Ga[P(H)Ar]$_3$, or the corresponding indium analogues respectively, while the reaction of $MCl_3$ with one equivalent of $Bu^t_2ELi$ and two equivalents of RLi resulted in dimeric phosphido- or arsenido-bridged compounds of the type $[M(u-EBu^t_2)R_2]_2$ (M=Al, Ga, In; E=P, As; R=Me, Bu$^n$).

Examples related to the present invention include: (i) synthesis of the first per-(dialkyl-phosphido) and —(-dialkylarsenido) compounds of gallium and indium; (ii) synthesis of the first primary phosphido compounds of gallium and indium; and, (iii) the first structural information on dialkylphosphido- and dialkylarsenido-bridged aluminum, gallium and indium dimers.

The following scheme indicates the synthesis and structure of seven compounds of the present invention.

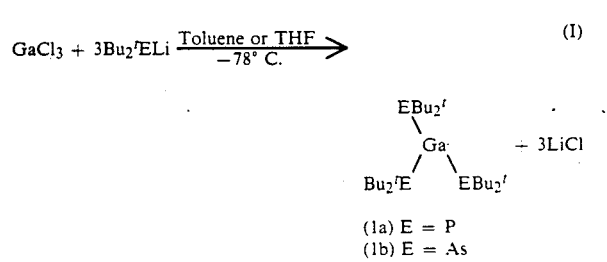

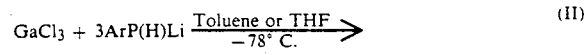

-continued $$Ga[P(H)Ar]_3 + 3LiCl$$

(2) Ar = 2,4,6 - Bu$_3^t$C$_6$H$_2$

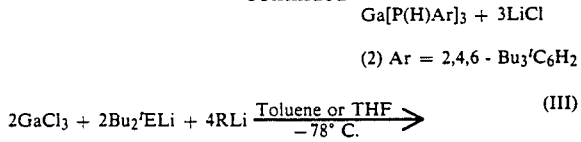

(III)

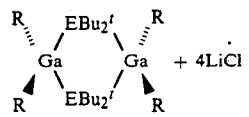 + 4LiCl (3a) E = P, R = Me  (4a) E = As, R = Me
(3b) E = P, R = Bu$^n$.  (4b) E = As, R = Bu$^n$ The use of bulky tertiary butyl (Bu$^t$) substituents permits the isolation of monomeric perphosphido and perarsenido gallium and indium compounds. Thus, treatment of GaCl$_3$ with three equivalents of Bu$^t_2$ELi (E=P, As) in toluene or tetrahydrofuran (THF) at $-78°$ C. results in high yields of Ga(PBu$^t_2$)$_3$, (1a), and Ga(AsBu$^t_2$)$_3$, (1b), as red, air-sensitive, crystalline solids, equation (I). The identification of (1a) and (1b) is based on spectroscopic and analytical data. Thus, the 70 eV electron impact mass spectrum (e.i.m.s.) of (1a) exhibits an apparent peak at m/z 504 and a fragmentation indicative of the sequential loss of Bu$_t$ and PBu$^t_2$ moieties. The e.i.m.s. of (1b) is very similar to that of (1a); however, in this case, the highest m/z peak (579) corresponds to M$^+$-Bu$^t$.

The primary phosphido compound, Ga[P(H)Ar]$_3$, (2) (Ar = 2,4,6-Bu$^t_3$C$_6$H$_2$) can be prepared in a similar fashion to (1a,b) using ArP(H)Li in place of Bu$^t_2$PLi, equation (II). The e.i.m.s. of (2) revealed a parent peak at m/z 900 and peaks of significant intensity at m/z 623 and 346 corresponding to the loss of one and two ArPH groups respectively. The presence of ArPH groups was confirmed by n.m.r. spectroscopy. X-Ray crystallographic studies of (2) have allowed us to discern the trigonal planar nature of the GaP$_3$ framework [av. Ga-P distance=2.34(I)A]. Similar skeletal geometries are proposed for (1a) and (1b).

The reaction of GaCl$_3$ with one equivalent of Bu$^t_2$ELi(E=P or As) and two equivalents of RLi(R =Me or Bu$^n$) in toluene or THF at $-78°$ C. afforded the dinuclear phosphido or arsenido bridged dimers [(3) and (4)] in good yields, following evaporation to dryness and recrystallization from hexane, equation (III). The aluminum and indium analogue, were prepared similarly. Complexes (3a), (3b), (4a), and (4b) were colorless, crystalline materials which may be recrystallized from hexane. In the solid state they were stable in the air for long periods (at least 24 h). Spectroscopic data were in accord with the structures determined by single crystal X-ray diffraction studies. Satisfactory chemical analyses were obtained for all new compounds. Compound (1a) $^1$H n.m.r. (C$_6$D$_6$ 360 MHz, ambient temperature) δ 1.55 (d, $^3J_{P-H}$ 12 Hz); $^{31}$P{$^1$H} n.m.r. 32.2 MHz, ambient temperature) δ54.8 (s). Compound (1b) $^1$H n.m.r. (C$_6$D$_6$, 90 MHz, ambient temperature) δ1.15 (s). Compound (2) $^1$H n.m.r. (C$_6$D$_6$, 90 MHz, ambient temperature) δ1.38 (9H, s, para Bu$^t$), 1.58 (18H, s. ortho Bu$^t$), 4.05 (1H, d, $^1J_{P-H}$ 216 Hz, PH), 7.48 (2H, s, CH); $^{31}$P n.m.r. (C$_6$D$_6$, 32.2 MHz, ambient temperature), δ-91.6(d,$^1J_{P-H}$215.6 Hz). Compound (3a) $^1$H n.m.r. (C$_6$D$_6$, 90 MHz, ambient temperature) δ0.28 (12H, t, $^3J_{P-H}$ 3 Hz, GaMe), 1.29 (36H, t, $^3J_{P-H}$ 6 Hz, But P); $^{31}$P{$^1$H} n.m.r. (C$_6$D$_6$, 32.2 MHz, ambient temperature (δ28.4 (s). Compound (3b) $^1$H n.m.r. (C$_6$D$_6$, 360 MHz, ambient temperature) δ1.06 (20H, m), 1.60(8H,m) 1.74 (8H, m) (all Bu$^n$), 1.40 (36H, t, $^3J_{P-H}$ 6 Hz, Bu$^t_2$P); $^{31}$P{$^1$H} n.m.r. (C$_6$D$_6$, 32.2 MHz, ambient temperature) δ32.9 (s). Compound (4a) $^1$H n.m.r. (C$_6$D$_6$ 90 MHz, ambient temperature) δ0.30 (12H, s, GaMe), 1.40 (36H, s, Bu$^t_2$As). Compound (4b) $^1$H n m.r. (C$_6$D$_6$, ambient temperature) δ1.04-1.06 (20H, m), 1.71 (8H,m) (all Bu$^n$), 1.40 (36H, s, Bu$^t_2$As).

Crystal data for (3a): C$_{20}$H$_{48}$Ga$_2$P$_4$, M=489.99, monoclinic, C2/c (No. 15), a=13.664(2),b=12.828(2), c=15.148(3) Å δ=104.221-(1)°, U=2573.8(5) Å$^3$, D$_c$=1.264 g cm$^{-3}$, Z=4, μ=22.11 cm$^{-1}$, number of reflections used =1279 [I>3σ(I)], (2259 unique measured), R=0.0531, R$_w$=0.0680. (3b): C$_{32}$H$_{72}$Ga$_2$P$_2$, M=658.32, monoclinic, P2$_1$/n (No. 1014), a=8.888(4), b=20.123(2), c=21.693(4) Å. β=95.555(3)°, U=3861.4(5) Å$^3$, D$_c$=1.132 g cm$^{-3}$, Z=4, number of reflections used=2018 [I>3σ(I)], (5966 unique measured), R=0.0595, R$_w$=0.0688. (4a): C$_{20}$H$_{48}$As$_2$Ga$_2$, M=577.89, monoclinic, C2/c (No. 15), a=13.856(2), b=12.882(1), c=15.356(3), β=104.398(1)°, U=2654.9(5) A$^3$, D$_c$=1.446 g cm$^{-3}$, Z=4, μ=44.95 cm$^{-1}$, number of reflections used=1396 [I >3 σ(I)], (2081 unique measured), R=0.0452, R$_w$=0.0630. (4b): C$_{32}$H$_{72}$As$_2$Ga$_2$, M=746.22, monoclinic, P2$_1$/n No. 1014), a=8.978(2), b=20.087(1), c=22.004(1) Å, β=96.023(3)°, U=3946.4(5)Å$^3$, D$_c$=1.256 g cm$^{-1}$, Z=4, μ=30.38 cm$^{-1}$, number of reflections used=2248 [I>3 σ(I)], (5392 unique measured), R=0.0530, R$_w$=0.0580 Data for all structures were collected on an Enraf-Nonius CAD-4 diffractometer, at 23±2° C., (Mo-K$_\alpha$)=0.71073 Å (graphite monochromator). Atomic coordinates, bond lengths and angles, and thermal parameters have been deposited at the Cambridge Crystallographic Data Centre.

Figure 2:
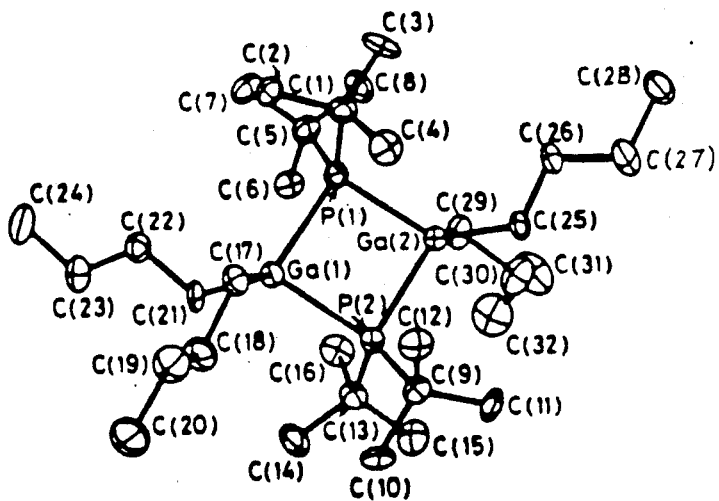
FIG. 2 shows an ORTEP view of [n-Bu$_2$Ga(t-Bu$_2$P)]$_2$; key bond lengths (Å) and angles (°): Ga(1)-P(1) 2.477(5), Ga(1)-P(2) 2.476(4), Ga(2)-P(1) 2.468(4), Ga(2)-P(2) 2.483(5), Ga(1)-C(17) 2.018(15), Ga(1)-C(21) 2.030(15), P(1)-C(1) 1.92(2), P(1)-Ga(1)-P(2) 86.7(1), P(1)-Ga(2)P(2) 86.7(2), Ga(1)-P(1)-Ga(2) 93.5(1), Ga(1)-P(2)-Ga(2) 93.1(2), P(1)-Ga(1)-C(17) 115.1(5), C(17)-Ga(1)-C(21) 107.0(6), C(1)-P(1)-C(5) 109.5(7). For (4b): As(1)-Ga(1) 2.552(3), As(1)-Ga(2) 2.548(3), As(2)-Ga(1) 2.551(2), As(2)-Ga(2) 2.557(3), Ga(1)-C(17) 2.02(2), As(1)-C(1) 2.06(2), Ga(1)-As(1)-Ga(2) 95.19(8), Ga(1)-As(2)-Ga(2) 94.96(8), As(1)-Ga(1)-As(2) 84.94(8), As(1)-Ga(2)-As(2) 84.91(8), As(1)-Ga(1)-C(17) 114.0(5), C(17)-Ga(1)-C(21) 110.9(7), C(1)-As(1)-C(5) 109.0(7).
Figure 3:
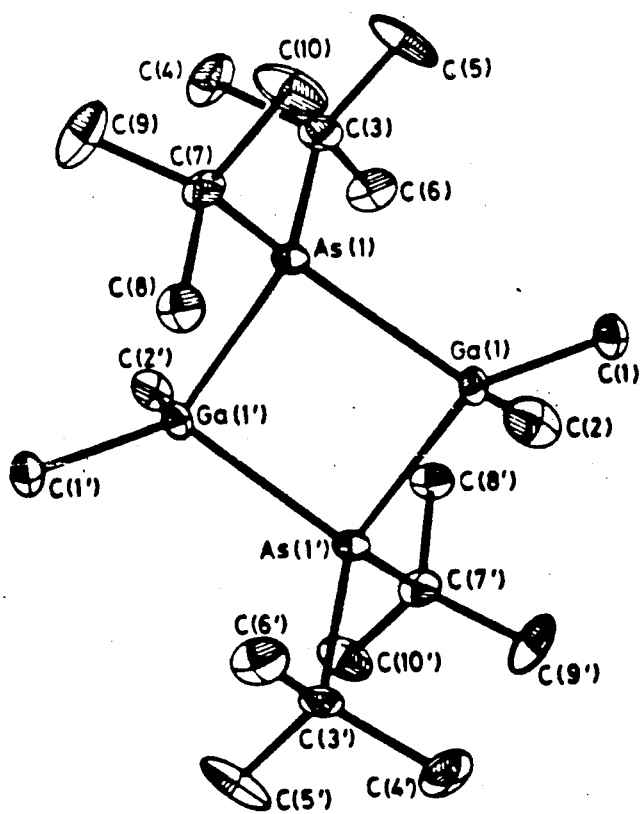
FIG. 3 shows an ORTEP View of (4a): key bond lengths (Å) and angles (°): As(1)-Ga(1) 2.541(1), As(1,)-Ga(1) 2.558(1), Ga(1)-C(1) 2.016(5), Ga(1)-C(2) 2.028(5), As(1)-C(3), 2.046(5), Ga(1)-As(1)-Ga(1,) 95.69(2), As(1)-Ga(1)-As(1,) 84.31, As(1)-Ga(1)-C(1) 115.1(2), As(1)-Ga(1)-C(2) 116.2(2), C(1)-Ga(1)-C(2) 109.3(3), C(3)-As(1)-C(7) 110.3(2). For (3a): Ga(1)-P(1,)

The methyl compounds (3a) and (4a) were isostructural, as were the n-butyl analogues (3b) and (4b). The molecular structures of (3b) and (4a) are shown in FIGS. 2 and 3 respectively. Compounds 3a, 3b, 4a and 4b were dimeric and feature two bridging Bu$^t_2$E entities and four terminal alkyl groups in each case. The central Ga$_2$E$_2$ core is essentially planar, unlike the puckered ring observed in the bulky thiolate complex. (Pr$^i$S-GaI$_2$)$_2$, in which a fold angle of 43.3(2)° was observed on the Ga . . . Ga' diagonal. The co-ordination about each Ga atom is roughly tetrahedral. Compounds (3a) and (4a) had a crystallographically imposed center of symmetry at the mid-point of the molecule. Examples of the indium and aluminum analogues of these compounds have been synthesized and they are characterized by the following; [Me$_2$Al(μ-t-Bu$_2$P)]$_2$; M.p. 295°-297° C. $^1$HNMR(C$_6$D$_6$, 361.08 MH$_2$) δ1.34, (t, $^3J_{P-H}$=6.5H$_2$, 36H); 0.00, (t, $^3J_{P-H}$=2.0H$_2$, 12H); $^{31}$P{$^1$H}NMR (C$_6$D$_6$, 32.38 MH$_2$), δ2.60 s. [Me$_2$In(μ-t-Bu$_2$P)]; M.p. 280°-300° C. NMR; $^1$H(C$_6$D$_6$, 361-08MH$_2$), δ1.30 (t, $^3J_{P-H}$=6.9H$_2$, 36H); 0.29 (t, $^3J_{P-H}$=1.8H$_2$, 12H); $^{31}$P{$^1$H} (C$_6$D$_6$, 32.38 MH$_2$) δ39.24 s. [Me$_2$Al(μ-t-Bu$_2$As)]$_2$; M.P. 276°-280° C.; NMR; $^1$H(C$_6$D$_6$, 300MH$_2$), δ1.39 (s, 36H); 0.01 (s, 12H) [Me$_2$In(μ-t-Bu$_2$As)]$_2$; M.p. 250°-251° C. (dec), MNR; $^1$H(C$_6$D$_6$, 300 MH$_2$) δ1.36 (s, 36H(; 0.33 (s, 12H) In(t-Bu$_2$P)$_3$; M.p. 165°-167° C. NMR $^1$H(C$_6$D$_6$, 300MH$_2$) δ1.51(d, J$_{P-H}$=11.0H$_2$) $^{31}$P{$^1$H} (C$_6$D$_6$, 121 MH$_2$) δ70.80 In(t-Bu$_2$As)$_3$; M.p. 134°-137° C.; $^1$H NMR (C$_6$D$_6$, 300 MH$_2$) δ1.54.

Further examples of these types of compounds are provided by the new compound [(t-Bu$_2$Sb)$_2$InCl]$_2$ (5)

which is obtained from the reaction of t-Bu₂SbSiMe₃ and InCl₃ according to the following equation.

$$4\ t\text{-}Bu_2SbSiMe_3 + 2InCl_3 \rightarrow [(t\text{-}Bu_2Sb)_2\ InCl]_2 + 4\ Me_3SiCl$$

NMR (C₆D₆, 25° C.): ¹H(300 MHz) 1.31 ppm (s, t$_{Bu}$): ¹³C (75.4 MHz) 35.2 ppm (s,CMe₃), 3.19 ppm (s, CCH₃).

The structure of 5 was determined by X-ray crystallography: C₁₆H₃₆ClInSb, M,=622.24, monoclinic, P2₁/n, a=11.854(6), b=12.767(4), c=16.505(4) Å, δ=106.75(2)°, V=2392.0 Å³, Z=4, D_c=1.728, μ=33.1 cm⁻¹ for Mo-K_α radiation (λ=0.71073 Å). Intensity data: Enraf-Nonium diffractometer, θ/2θ scan mode, 4207 reflections in the range 3.0≦2θ≦50.0°. The structure of 5 was solved by direct methods and refined (full matrix, least squares) by using 2965 reflections with I>3σ(I). The final residuals were R-0.050 and R_w=0.057.

Another example is the new compound [Cl₂GaSb(t-Bu)₂]₃ (6), which was synthesized from the reaction of t-Bu2SbSiMe₃ and GaCl₃. An X-ray structure determination revealed a boat type conformation for the Ga₃Sb₃ ring.

Crystal data: (6) C₂₄H₅₄Cl₆Ga₃Sb₃,M=1129.83, monoclinic, space group P2₁/m. (No. 11), a=8.871 (1), b=23.630 (2), c=11.861 (2) Å, β=106.56(3)°, U=2383.2 Å³, D_c=1.574 g çm⁻³, Z=2, λ(Mo-K_α) =0.71073 Å, μ(Mo-K₆₀) = 37.08 cm⁻¹. A total of 4290 unique reflections was collected as described above for 5. Solution and refinement of the structure as per 5 but using 3009 reflections with I>3 σ(I) afforded final R and R_w values of 0.0853 and 0.1022 respectively.

The average In-As bond lengths for 5 (planar form, 2.679 (2); puckered form, 2.669(3)Å are slightly longer than the sum of covalent radii (2.64 Å)is close to the sum of covalent radii (2.66 Å) and to the bond distance in GaSb (2.649 Å). The average Ga-Sb bond length for 6 (2.661(2) Å) is close to the sum of covalent radii (2.66 Å) and to the bond distance in GaSb (2.649 Å).

A compound of formula ]R₂MER'R"]_n where R=t-Bu, M=Ga, E=P, R'=hydrogen and R"=cyclopentyl and n=2, is given by the following example.

Reaction of GaCl₃ with two equivalents of t-BuLi and one equivalent of the monolithiated primary phosphine LiP(H)(cyclopentyl) yields [t-Bu₂GaP(H)(cyclopentyl)]₂ as colorless crystals which are soluble in hexane. mp:202°-206° C.(dec) ¹H NMR(C₆D₆, 300 MHz) δ1.31 (br. mult.) ³¹P{¹H} NMR(C₆D₆, 121 MHz), δ-90.27 (area 2), δ-94.51 (area 1) ³¹P NMR: δ- 90.27 (br d of d ¹ J$_{P-H}$=175Hz, ²J$_{P-H}$=105Hz) δ94.51 (br d of d ¹J$_{P-H}$=178Hz, ²J$_{P-H}$=106Hz) X-ray data: C₂₆H₅₆Ga₂P₂, Mr=570.1. monoclinic, C2/m, a=16.736(3) Å, b=11.586(1) Å, c=8.413(2) Å, β=104.62(1)°, U=1578.6(5) Å³, Z=2, D_calc=1.728 g cm⁻³, μ=18.11 cm⁻¹, for MoK_α radiation (λ=0.71073 Å). Intensity data Enraf-nonu CAD-4 diffractometer, θ/2θ scan mode 1447 reflections in the range 3°<2-θ<50°, the structure was solved by direct methods (full matrix, least squares) by using 1447 reflections with I>3σ(I). The final residuals were R=0.050 and R_w=0.057.

Changes may be made in the substitution, operation and arrangement of the various compounds, steps, and procedures described herein without departing from the concept and scope of the invention as defined in the following claims.

What is claimed is:

1. A compound having the formula:

{R₂M(ER'R")}n wherein
   M is gallium,
   E is antimony,
   R is chloride, R' and R" are t-butyl; and n is 2
   wherein M and E are bound by direct sigma bonding.

2. A compound having the formula:

{R₂M(ER'R")}₂ where
   R is methyl;
   M is gallium;
   E is phorsphorus;
   R' is t-butyl; and
   R" is t-butyl.

3. A compound having the formula:

{R₂M(ER'R")}₂ where
   R is n-butyl;
   M is gallium;
   E is phosphorus:
   R' is t-butyl; and
   R" is t-butyl.

4. A compound having the formula:

{R₂M(ER'R")}₂ where
   R is methyl;
   M is gallium;
   E is arsenic;
   R' is t-butyl; and
   R" is t-butyl.

5. A compound having the formula:

{R₂M(ER'R")}₂ where
   R is n-butyl;
   M is gallium;
   E is arsenic;
   R' is t-butyl; and
   R" is t-butyl.

6. A compound having the formula:

{R₂M(ER'R")}₂ where
   R is t-butyl;
   M is gallium;
   E is phosphorous;
   R' is hydrogen; and
   R" is cyclopentyl.

7. A compound having the formula:

{R₂M(ER'R")}₂ where
   R is methyl;
   M is aluminum;
   E is phorphorous;
   R' is t-butyl; and R'' is t-butyl.

8. A compound having the formula:

$$\{R_2M(ER'R'')\}_2$$

where
R is methyl;
M is indium;
E is phosphorus;
R' is t-butyl; and
R'' is t-butyl.

9. A compound having the formula:

$$\{R_2M(ER', R'')\}_2$$

where
R is methyl;
M is indium;
E is arsenic
R' is t-butyl, and "R" is t-butyl.

* * * * *

UNITED STATES PATENT AND TRADEMARK OFFICE
CERTIFICATE OF CORRECTION

PATENT NO. : 5,047,565

DATED : September 10, 1991

INVENTOR(S) : Richard A. Jones, Alan H. Cowley, John G. Ekerdt

It is certified that error appears in the above-identified patent and that said Letters Patent is hereby corrected as shown below:

In claim 2, column 10, line 17 delete the term "phorsphorus" and insert the term --phosphorus-- therefor.

In claim 7, column 10, line 66, delete the term "phorsphorus" and insert the term --phosphorus-- therefor.

Signed and Sealed this

Thirtieth Day of March, 1993

Attest:

STEPHEN G. KUNIN

*Attesting Officer*  *Acting Commissioner of Patents and Trademarks*